United States Patent
Lee et al.

(10) Patent No.: US 11,564,599 B2
(45) Date of Patent: Jan. 31, 2023

(54) APPARATUS AND METHOD FOR OBTAINING INDIVIDUALIZED UNIT SPECTRUM, AND APPARATUS AND METHOD FOR ESTIMATING BIOLOGICAL COMPONENT

(71) Applicant: SAMSUNG ELECTRONICS CO., LTD., Suwon-si (KR)

(72) Inventors: So Young Lee, Daejeon (KR); Sang Kon Bae, Seongnam-si (KR); Jae Wook Shim, Yongin-si (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 1143 days.

(21) Appl. No.: 16/161,998

(22) Filed: Oct. 16, 2018

(65) Prior Publication Data

US 2019/0117136 A1    Apr. 25, 2019

(30) Foreign Application Priority Data

Oct. 19, 2017  (KR) .......................... 10-2017-0136132

(51) Int. Cl.
*A61B 5/145*    (2006.01)
*A61B 5/00*    (2006.01)
(Continued)

(52) U.S. Cl.
CPC ........ *A61B 5/14532* (2013.01); *A61B 5/0075* (2013.01); *A61B 5/1455* (2013.01);
(Continued)

(58) Field of Classification Search
CPC .............. A61B 5/14532; A61B 5/0075; A61B 5/1455; A61B 5/6802; A61B 5/681;
(Continued)

(56) References Cited

U.S. PATENT DOCUMENTS

| 5,957,841 A | 9/1999 | Maruo et al. |
| 6,841,389 B2 | 1/2005 | Novikov et al. |

(Continued)

FOREIGN PATENT DOCUMENTS

| CN | 1697967 A | 11/2005 |
| EP | 3 329 848 A1 | 6/2018 |

(Continued)

OTHER PUBLICATIONS

Robertson, et al., "Blood Glucose Prediction Using Artificial Neural Networks Trained with the AIDA Diabetes Simulator: A Proof-of-Concept Pilot Study", 2011, Journal of Electrical and Computer Engineering, vol. 2011, Article ID 681786, 12 pages total.

(Continued)

*Primary Examiner* — Dominic J Bologna
(74) *Attorney, Agent, or Firm* — Sughrue Mion, PLLC

(57) ABSTRACT

A apparatus for obtaining an individualized unit spectrum includes: a spectrum obtainer configured to obtain a first biological spectrum from a subject at a first measurement time, and obtain a second biological spectrum from the subject at a second measurement time; and a processor configured to extract the individualized unit spectrum from the first biological spectrum and the second biological spectrum, based on a predetermined unit spectrum of a target component.

20 Claims, 16 Drawing Sheets

(51) Int. Cl.
  *A61B 5/1455*  (2006.01)
  *G16H 50/20*  (2018.01)
  *G01N 21/3577*  (2014.01)
  *G01N 21/47*  (2006.01)

(52) U.S. Cl.
  CPC ..... *G01N 21/3577* (2013.01); *G01N 21/4795* (2013.01); *G16H 50/20* (2018.01)

(58) Field of Classification Search
  CPC ............... A61B 5/7203; A61B 5/7235; A61B 5/7271; G01N 21/3577; G01N 21/4795; G01N 21/25; G16H 50/20
  See application file for complete search history.

(56) References Cited

U.S. PATENT DOCUMENTS

| | | | |
|---|---|---|---|
| 6,990,364 | B2 | 1/2006 | Rutchi et al. |
| 7,010,336 | B2 | 3/2006 | Lorenz et al. |
| 7,133,710 | B2 | 11/2006 | Acosta et al. |
| 7,165,452 | B2 | 1/2007 | Kobayashi |
| 7,333,841 | B2 | 2/2008 | Maruo et al. |
| 7,438,855 | B2 | 10/2008 | Sota et al. |
| 7,460,895 | B2 | 12/2008 | Arnold et al. |
| 9,448,164 | B2 | 9/2016 | Gulati et al. |
| 2003/0031597 | A1 | 2/2003 | Sota et al. |
| 2003/0216627 | A1* | 11/2003 | Lorenz ................. A61B 5/1455 600/322 |
| 2004/0068163 | A1 | 4/2004 | Rutchi et al. |
| 2004/0142402 | A1 | 7/2004 | Maruo et al. |
| 2011/0071365 | A1* | 3/2011 | Lee ........................ G16H 50/70 600/300 |
| 2012/0035442 | A1* | 2/2012 | Barman ................. G01J 3/0208 600/316 |
| 2017/0079565 | A1 | 3/2017 | Choi et al. |
| 2018/0064378 | A1 | 3/2018 | Park et al. |
| 2018/0146899 | A1 | 5/2018 | Lee et al. |

FOREIGN PATENT DOCUMENTS

| | | | |
|---|---|---|---|
| JP | 2003-42948 | A | 2/2003 |
| JP | 2003-144421 | A | 5/2003 |
| JP | 2010-66280 | A | 3/2010 |
| JP | 4472794 | B2 | 6/2010 |
| KR | 10-2004-0020878 | A | 3/2004 |
| KR | 10-2005-0078924 | A | 8/2005 |
| KR | 10-2017-0035675 | A | 3/2017 |
| KR | 10-2018-0027006 | A | 3/2018 |
| WO | 2004/081524 | A2 | 9/2004 |

OTHER PUBLICATIONS

Pappada, et al., "Development of a Neural Network for Prediction of Glucose Concentration in Type 1 Diabetes Patients", Sep. 2008, Journal of Diabetes Science and Technology, vol. 2, Issue 5, 10 pages total.
Rishikesh Pandey et al., "Noninvasive Monitoring of Blood Glucose with Raman Spectroscopy", Account of Chemical Research, Feb. 21, 2017, vol. 50, No. 2, pp. 264-272, XP055564367. (18 pages total).
Maarten J. Scholtes-Timmerman, MSc. et al., "Raman Spectroscopy as a Promising Tool for Noninvasive Point-of-Care Glucose Monitoring", Journal of Diabetes Science and Technology, Jan. 1, 2014, vol. 8, No. 5, pp. 974-979, XP055564363. )6 pages total).
Communication dated Mar. 14, 2019 issued by the European Patent Office in counterpart European Patent Application No. 18200705.4.
Communication dated Mar. 2, 2022 by the State Intellectual Property Office of P.R. China in Chinese Patent Application No. 201811206668.6.

* cited by examiner

APPARATUS AND METHOD FOR OBTAINING INDIVIDUALIZED UNIT SPECTRUM, AND APPARATUS AND METHOD FOR ESTIMATING BIOLOGICAL COMPONENT

CROSS-REFERENCE TO RELATED APPLICATION(S)

This application claims priority from Korean Patent Application No. 10-2017-0136132, filed on Oct. 19, 2017, in the Korean Intellectual Property Office, the disclosure of which is incorporated herein by reference in its entirety.

BACKGROUND

1. Field

Apparatuses and methods consistent with exemplary embodiments relate to estimating biological components in a non-invasive manner, and more particularly to obtaining an individualized unit spectrum in consideration of optical characteristics of individuals, and estimating biological components based on the individualized unit spectrum.

2. Description of the Related Art

Diabetes is a chronic disease that causes various complications and can be hardly cured, such that people with diabetes are advised to check their blood glucose regularly to prevent complications. In particular, when insulin is administered to control blood glucose, the blood glucose levels have to be closely monitored to avoid hypoglycemia and control insulin dosage. An invasive method of finger pricking is generally used to measure blood glucose levels. However, while the invasive method may provide high reliability in measurement, it may cause pain and inconvenience as well as an increased risk of disease infections due to the use of a lancet for the finger pricking. Recently, research has been conducted on non-invasive measurements of blood glucose by using a spectrometer without collecting blood.

SUMMARY

Exemplary embodiments address at least the above problems and/or disadvantages and other disadvantages not described above. Also, the exemplary embodiments are not required to overcome the disadvantages described above, and may not overcome any of the problems described above.

One or more exemplary embodiments provide an apparatus and method for obtaining an individualized unit spectrum in consideration of optical characteristics of individuals, and an apparatus and method for estimating a biological component.

According to an aspect of an exemplary embodiment, there is provided an apparatus for obtaining an individualized unit spectrum including: a spectrum obtainer configured to obtain a first biological spectrum from a subject at a first measurement time, and obtain a second biological spectrum from the subject at a second measurement time; and a processor configured to extract the individualized unit spectrum from the first biological spectrum and the second biological spectrum, based on a predetermined unit spectrum of a target component.

The processor may include a candidate spectrum extractor configured to extract at least one candidate spectrum from the first biological spectrum and the second biological spectrum.

The candidate spectrum extractor may further be configured to extract the at least one candidate spectrum based on at least one of principal component analysis (PCA), independent component analysis (ICA), non-negative matrix factorization (NMF), and auto-encoding (AE).

The processor may further include: a candidate spectrum selector configured to select a candidate spectrum, associated with the target component, from among the extracted at least one candidate spectrum; and an individualized unit spectrum extractor configured to scale the selected candidate spectrum based on the predetermined unit spectrum, and extract the scaled candidate spectrum as the individualized unit spectrum.

The candidate spectrum selector may be further configured to select the candidate spectrum based on at least one of a shape of the candidate spectrum and a variation over time in the candidate spectrum.

The candidate spectrum selector may be further configured to select the candidate spectrum in response to the candidate spectrum satisfying at least one of a first condition under which a first similarity between the candidate spectrum and the predetermined unit spectrum exceeds a first threshold, a second condition under which a second similarity between a variation over time in the candidate spectrum and a step function exceeds a second threshold, and a third condition under which a product of the first similarity and the second similarity exceeds a third threshold.

The candidate spectrum selector may use a similarity calculation method or a statistical test, wherein the similarity calculation method may include at least one of Euclidean distance, Manhattan Distance, Cosine Distance, Mahalanobis Distance, Jaccard Coefficient, Extended Jaccard Coefficient, Pearson's Correlation Coefficient, and Spearman's Correlation Coefficient, and the statistical test may include at least one of f-test, t-test, and z-test.

In response to a plurality of candidate spectrums being selected by the candidate spectrum selector, the individualized unit spectrum extractor may be configured to generate an average candidate spectrum by averaging the selected plurality of candidate spectrums, and scale the generated average candidate spectrum to correspond to the predetermined unit spectrum.

The apparatus may further include a preprocessor configured to remove noise from the first biological spectrum and the second biological spectrum.

The preprocessor may be further configured to use at least one of asymmetric least square (ALS), detrend, multiplicative scatter correction (MSC), extended multiplicative scatter correction (EMSC), standard normal variate (SNV), mean centering (MC), fourier transform (FT), orthogonal signal correction (OSC), and Savitzky-Golay smoothing (SG).

The processor may include: a subtractor configured to subtract the first biological spectrum from the second biological spectrum to obtain a subtracted spectrum; and an individualized unit spectrum extractor configured to scale the subtracted spectrum to correspond to the predetermined unit spectrum of the target component, and extract the scaled subtracted spectrum as the individualized unit spectrum.

The processor may be further configured to select a method from among: a first method of extracting the individualized unit spectrum using principal component analysis (PCA); a second method of extracting the individualized unit spectrum using independent component analysis (ICA); a third method of extracting the individualized unit spectrum using non-negative matrix factorization (NMF); a fourth method of extracting the individualized unit spectrum using auto-encoding (AE); and a fifth option of method the individualized unit spectrum by subtracting the first biological spectrum from the second biological spectrum, wherein the processor may be further configured to extract the individualized unit spectrum based on the selected method.

The target component may include a blood component and a skin component of the subject, wherein the blood component may include at least one of blood glucose, cholesterol, triglyceride, proteins, and uric acid; and the skin component may include at least one of proteins including collagen, keratin, and elastin, and body fat.

According to an aspect of another exemplary embodiment, there is provided a method of obtaining an individualized unit spectrum, the method including: obtaining a first biological spectrum from a subject at a first measurement time, and obtain a second biological spectrum from the subject at a second measurement time; and extracting the individualized unit spectrum from the first biological spectrum and the second biological spectrum, based on a predetermined unit spectrum of a target component.

The extracting the individualized unit spectrum may include: extracting at least one candidate spectrum from the first biological spectrum and the second biological spectrum; selecting a candidate spectrum, associated with the target component, from the extracted at least one candidate spectrum; scaling the selected candidate spectrum based on the predetermined unit spectrum; and extracting the scaled candidate spectrum as the individualized unit spectrum.

The extracting the candidate spectrum may include extracting the candidate spectrum based on at least one of principal component analysis (PCA), independent component analysis (ICA), non-negative matrix factorization (NMF), and auto-encoding (AE).

The selecting the candidate spectrum associated with the target component may include selecting the candidate spectrum based on at least one of a shape of the candidate spectrum and a variation over time in the candidate spectrum.

The selecting the candidate spectrum associated with the target component may include selecting the candidate spectrum in response to the candidate spectrum satisfying at least one of a first condition under which a first similarity between the candidate spectrum and the predetermined unit spectrum exceeds a first threshold, a second condition under which a second similarity between a variation over time in the candidate spectrum and a step function exceeds a second threshold, and a third condition under which a product of the first similarity and the second similarity exceeds a third threshold.

The selecting the candidate spectrum associated with the target component may include selecting the candidate spectrum based on a similarity calculation method or a statistical test, wherein the similarity calculation method may include at least one of Euclidean distance, Manhattan Distance, Cosine Distance, Mahalanobis Distance, Jaccard Coefficient, Extended Jaccard Coefficient, Pearson's Correlation Coefficient, and Spearman's Correlation Coefficient, and the statistical test may include at least one of f-test, t-test, and z-test.

The scaling the selected candidate spectrum may include, in response to a plurality of candidate spectrums being selected, generating an average candidate spectrum by averaging the selected plurality of candidate spectrums, and scaling the generated average candidate spectrum to correspond to the predetermined unit spectrum.

The method may further include removing noise from the first biological spectrum and the second biological spectrum.

The removing the noise may include removing the noise based on at least one of asymmetric least square (ALS), detrend, multiplicative scatter correction (MSC), extended multiplicative scatter correction (EMSC), standard normal variate (SNV), mean centering (MC), fourier transform (FT), orthogonal signal correction (OSC), and Savitzky-Golay smoothing (SG).

The extracting the individualized unit spectrum may include: subtracting the first biological spectrum from the second biological spectrum to obtain a subtracted spectrum; scaling the subtracted spectrum to correspond to the predetermined unit spectrum of the target component; and extracting the scaled subtracted spectrum as the individualized unit spectrum.

The method may further include selecting a method from among: a first method of extracting the individualized unit spectrum using principal component analysis (PCA); a second method of extracting the individualized unit spectrum using independent component analysis (ICA); a third method of extracting the individualized unit spectrum using non-negative matrix factorization (NMF); a fourth method of extracting the individualized unit spectrum using auto-encoding (AE); and a fifth method of extracting the individualized unit spectrum by subtracting the first biological spectrum from the second biological spectrum, wherein the extracting the individualized unit spectrum comprises extracting the individualized unit spectrum based on the selected method.

The target component may include a blood component and a skin component, wherein the blood component may include at lease one of blood glucose, cholesterol, triglyceride, proteins, and uric acid; and the skin component may include at least one of proteins including collagen, keratin, and elastin, and body fat.

According to an aspect of another exemplary embodiment, there is provided an apparatus for estimating a biological component, the apparatus including: a spectrometer configured to measure a biological spectrum by emitting a light onto a user and receiving the light reflected or scattered from the user, and a processor configured to estimate a biological component based on the measured biological spectrum and an individualized unit spectrum, wherein the individualized unit spectrum may be extracted from a first biological spectrum that is measured from the user at a first measurement time, and a second biological spectrum that is measured from the subject at a second measurement time.

The spectrometer may use at least one of infrared spectroscopy or Raman spectroscopy.

The processor may include: a model generator configured to generate a biological component estimation model based on a background spectrum of the user and the individualized unit spectrum; and a biological component estimator configured to estimate the biological component based on the measured biological spectrum and the biological component estimation model.

According to a predetermined interval or a user's request, the spectrometer may be further configured to measure the background spectrum from the user at the first measurement time.

According to an aspect of another exemplary embodiment, there is provided an apparatus for measuring a biological component including: a spectrometer configured to obtain, from a subject, a first biological spectrum at a first measurement time and a second biological spectrum at a second measurement time, the first measurement time having a longer elapsed time than the second measurement time from a point in time when the subject consumes food; a storage configured to store a reference spectrum of blood glucose concentration that changes over time; and a processor configured to obtain an individualized unit spectrum based a comparison between the reference spectrum and a feature value extracted from the first biological spectrum and the second biological spectrum.

The processor may be further configured to extract, as the feature value, a principal component by performing principal component analysis on the first biological spectrum and the second biological spectrum.

The processor may be further configured to extract, as the feature value, a weight vector by performing auto-encoding on the first biological spectrum and the second biological spectrum.

BRIEF DESCRIPTION OF THE DRAWINGS

The above and/or other aspects will be more apparent by describing certain exemplary embodiments, with reference to the accompanying drawings, in which.

DETAILED DESCRIPTION

Figure 1:
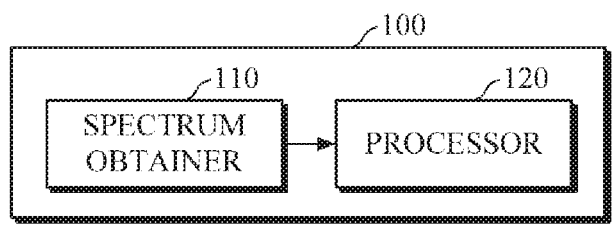
FIG. 1 is a block diagram illustrating an apparatus for obtaining an individualized unit spectrum according to an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

Process steps described herein may be performed differently from a specified order, unless a specified order is clearly stated in the context of the disclosure. That is, each step may be performed in a specified order, at substantially the same time, or in a reverse order.

Further, the terms used throughout this specification are defined in consideration of the functions according to exemplary embodiments, and can be varied according to a purpose of a user or manager, or precedent and so on. Therefore, definitions of the terms should be made on the basis of the overall context.

It will be understood that, although the terms first, second, etc. may be used herein to describe various elements, these elements should not be limited by these terms. These terms are only used to distinguish one element from another. Any references to singular may include plural unless expressly stated otherwise. In the present specification, it should be understood that the terms, such as 'including' or 'having.' etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, or all of a, b, and c.

Further, components that will be described in the specification are discriminated merely according to functions mainly performed by the components. That is, two or more components which will be described later can be integrated into a single component. Furthermore, a single component which will be explained later can be separated into two or more components. Moreover, each component which will be described can additionally perform some or all of a function executed by another component in addition to the main function thereof. Some or all of the main function of each component which will be explained can be carried out by another component. Each component may be implemented as hardware, software, or a combination of both.

A unit spectrum described in the present disclosure refers to a spectrum of a material per unit concentration (e.g., 1 mM), and an individualized unit spectrum refers to a unit spectrum obtained in consideration of optical characteristics of each individual.

FIG. 1 is a block diagram illustrating an apparatus for obtaining an individualized unit spectrum according to an exemplary embodiment. The apparatus 100 may be embedded in an electronic device. In particular, examples of the electronic device may include a cellular phone, a smartphone, a tablet PC, a laptop computer, a personal digital assistant (PDA), a portable multimedia player (PMP), a navigation, an MP3 player, a digital camera, a wearable device, and the like; and examples of the wearable device may include a wristwatch-type wearable device, a wristband-type wearable device, a ring-type wearable device, a waist belt-type wearable device, a necklace-type wearable device, an ankle band-type wearable device, a thigh band-type wearable device, a forearm band-type wearable device, and the like. However, the electronic device is not limited thereto, and the wearable device is neither limited thereto.

Referring to FIG. 1, the apparatus 100 for obtaining an individualized unit spectrum includes a spectrum obtainer 110 and a processor 120.

The spectrum obtainer 110 may obtain a biological spectrum (hereinafter referred to as a first biological spectrum) measured in the case where there is a small amount of a target component in a body, and a biological spectrum (hereinafter referred to as a second biological spectrum) measured in the case where there is a large amount of a target component in a body. The target component may include a blood component, including blood glucose, cholesterol, triglyceride, protein, uric acid, and the like, and a skin component including collagen, keratin, elastin, and the like.

In one exemplary embodiment, the spectrum obtainer 110 may obtain the first biological spectrum and the second biological spectrum from an external device which measures and/or stores biological spectrums. In particular, the spectrum obtainer 110 may use various communication techniques, such as Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WiFi communication, Radio Frequency Identification (RFID) communication, 3G communication, 4G communication, 5G communication, and the like.

In another exemplary embodiment, in the case where there is a small amount of a target component in a body (e.g., in an empty stomach state if a target component is blood glucose), the spectrum obtainer 110 may obtain the first biological spectrum by emitting light onto skin and by receiving light reflected or scattered from the skin; and in the case where there is a large amount of a target component (e.g., after intake of sugar if a target component is blood glucose), the spectrum obtainer 110 may obtain the second biological spectrum by emitting light onto skin and by receiving light reflected or scattered from the skin. For example, the spectrum obtainer 100 may obtain the first biological spectrum at a first measurement time (e.g., 5 hours after food consumption), and may obtain the second biological spectrum at a second measurement time (e.g., within 2 hours after food consumption). The spectrum obtainer 110 may include a light source to emit light onto skin, and a photodetector to obtain a biological spectrum by receiving light reflected or scattered from the skin. For example, the spectrum obtainer 110 may be realized as an optical spectrometer.

The light source in the spectrum obtainer 110 may emit near infrared rays (NIR) or mid infrared rays (MIR). However, wavelengths of light to be emitted by the light source may vary according to a purpose of measurement or the types of target component to be analyzed. Further, the light source may include a single light-emitting body, or may be formed as an array of a plurality of light-emitting bodies. The light source may include a light emitting diode (LED), a laser diode, a fluorescent body, and the like. The photodetector may include a photo diode, a photo transistor (PTr), a charge-coupled device (CCD), and the like. The photodetector may include a single device, and may be formed as an array of a plurality of devices. There may be various numbers and arrangements of light sources and photodetectors, and the number and arrangement thereof may vary according to the types of target component, a purpose of use, the size and shape of the electronic device in which the apparatus 100 is embedded, and the like.

The processor 120 may process various signals and operations related to the obtaining of an individualized unit spectrum by the apparatus 100.

According to predetermined intervals or a user's request, the processor 120 may control the spectrum obtainer 110 to obtain the first biological spectrum and the second biological spectrum, and may extract an individualized unit spectrum, corresponding to a unit spectrum of a target component, from the obtained first biological spectrum and second biological spectrum. Here, various intervals may be set by a user to repeatedly obtain the first biological spectrum and the second biological spectrum. The unit spectrum may be experimentally derived in advance and stored in the apparatus 100.

For example, the processor 120 may extract an individualized unit spectrum from the first biological spectrum or the second biological spectrum by using a feature extraction method, or may extract an individualized unit spectrum by subtracting the first biological spectrum from the second biological spectrum. In this case, the feature extraction method may include principal component analysis (PCA), independent component analysis (ICA), non-negative matrix factorization (NMF), auto-encoding (AE), and the like.

Figure 2:
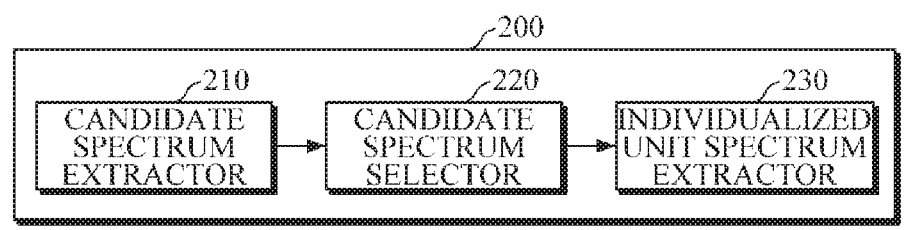
FIG. 2 is a block diagram illustrating a processor according to an exemplary embodiment.

FIG. 2 is a block diagram illustrating a processor according to an exemplary embodiment. The processor 200 of FIG. 2 may be an example of the processor 120 of FIG. 1.

Referring to FIG. 2, the processor 200 includes a candidate spectrum extractor 210, a candidate spectrum selector 220, and an individualized unit spectrum extractor 230.

The candidate spectrum extractor 210 may extract at least one candidate spectrum from the first biological spectrum and the second biological spectrum by using a feature extraction method. In this case, as described above, the feature extraction method may include principal component analysis (PCA), independent component analysis (ICA), non-negative matrix factorization (NMF), auto-encoding (AE), and the like, as described above.

The candidate spectrum selector 220 may select a candidate spectrum, associated with a target component, from among the extracted at least one candidate spectrum. In one exemplary embodiment, the candidate spectrum selector 220 may select a candidate spectrum, which satisfies predetermined requirements, as a candidate spectrum associated with a target component based on the shape of a candidate spectrum and/or a variation over time in a candidate spectrum. In particular, the predetermined requirements may include a requirement for a similarity (hereinafter referred to as a first similarity) between a candidate spectrum and a unit spectrum of a target component to exceed a predetermined threshold (hereinafter referred to as a first threshold), a requirement for a similarity (hereinafter referred to as a second similarity) between a variation over time in a candidate spectrum and a step function to exceed a predetermined threshold (hereinafter referred to as a second threshold), a requirement for a value obtained by multiplying the first similarity and the second similarity to exceed a predetermined threshold (hereinafter referred to as a third threshold), and the like. The step function schematically represents an actual change in the target component, and information on a unit spectrum of a target component may be pre-stored in an internal or external database. The candidate spectrum selector 220 may select a candidate spectrum, which satisfies at least one of the aforementioned predetermined requirements, from among the extracted at least one candidate spectrum.

For example, the candidate spectrum selector 220 may use a similarity calculation method, such as Euclidean distance, Manhattan Distance, Cosine Distance, Mahalanobis Distance, Jaccard Coefficient, Extended Jaccard Coefficient, Pearson's Correlation Coefficient. Spearman's Correlation Coefficient, and the like, or a statistical test such as f-test, t-test, z-test, and the like.

The individualized unit spectrum extractor 230 may scale the selected candidate spectrum to correspond to a unit spectrum of a target component, and may extract the scaled candidate spectrum as an individualized unit spectrum. The candidate spectrum is extracted from the first biological spectrum and the second biological spectrum regardless of a concentration of a target component, such that the individualized unit spectrum extractor 230 may extract an individualized unit spectrum, corresponding to a unit spectrum, by scaling the selected candidate spectrum to a range of a unit spectrum. The scaled selected candidate spectrum may have substantially the same amplitude as the unit spectrum of the target component.

In addition, the candidate spectrum selector 220 may select a plurality of candidate spectrums. In this case, the individualized unit spectrum extractor 230 may generate an average candidate spectrum by averaging the selected plurality of candidate spectrums, may scale the generated average candidate spectrum to correspond to a unit spectrum, and may extract the scaled average candidate spectrum as an individualized unit spectrum.

Figure 3:
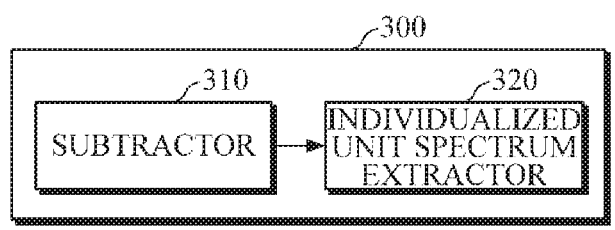
FIG. 3 is a block diagram illustrating a processor according to another exemplary embodiment.

FIG. 3 is a block diagram illustrating a processor according to another exemplary embodiment. The processor 300 of FIG. 3 may be another example of the processor 120 of FIG. 1.

Referring to FIG. 3, the processor 300 includes a subtractor 310 and an individualized unit spectrum extractor 320.

The subtractor 310 may subtract the first biological spectrum from the second biological spectrum. In one exemplary embodiment, in the case where there are a plurality of second biological spectrums and a plurality of first biological spectrums, the subtractor 310 may calculate an average second biological spectrum and an average first biological spectrum, and may subtract the calculated average first biological spectrum from the calculated average second biological spectrum.

The individualized unit spectrum extractor 320 may scale the spectrum, generated as a result of the subtraction by the subtractor 310, to correspond to a unit spectrum of a target component, and may extract the scaled spectrum as the individualized unit spectrum.

Figure 4:
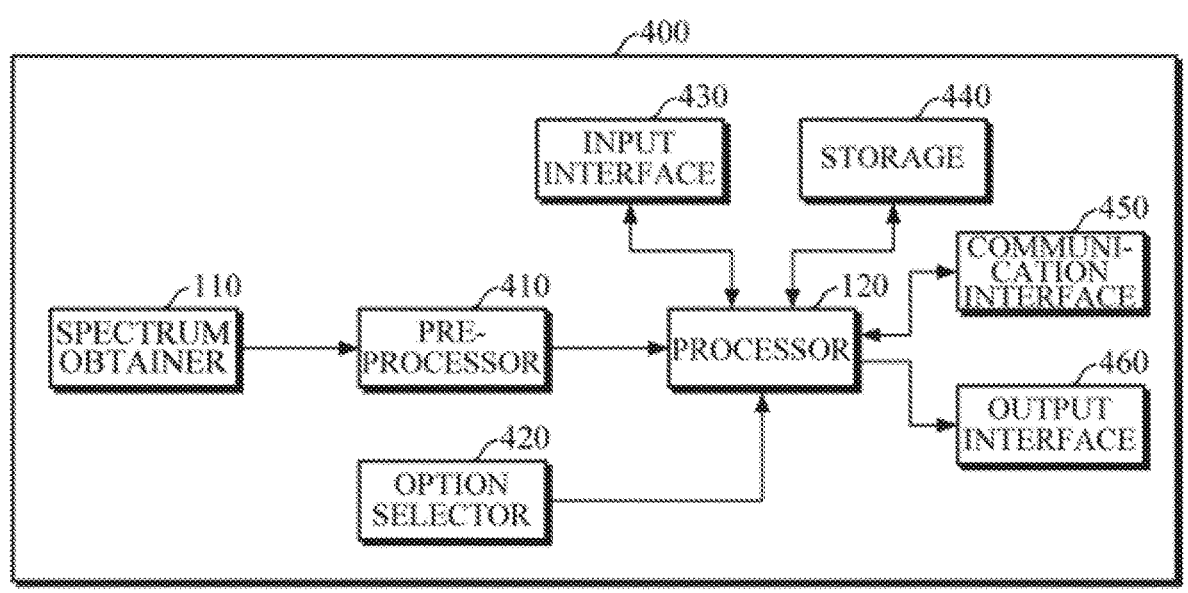
FIG. 4 is a block diagram illustrating an apparatus for obtaining an individualized unit spectrum according to another exemplary embodiment.

FIG. 4 is a block diagram illustrating an apparatus for obtaining an individualized unit spectrum according to another exemplary embodiment. The apparatus 400 may be embedded in an electronic device. In particular, examples of the electronic device may include a cellular phone, a smartphone, a tablet PC, a laptop computer, a personal digital assistant (PDA), a portable multimedia player (PMP), a navigation, an MP3 player, a digital camera, a wearable device, and the like; and examples of the wearable device may include a wristwatch-type wearable device, a wristband-type wearable device, a ring-type wearable device, a waist belt-type wearable device, a necklace-type wearable device, an ankle band-type wearable device, a thigh band-type wearable device, a forearm band-type wearable device, and the like. However, the electronic device is not limited thereto, and the wearable device is neither limited thereto.

Referring to FIG. 4, the apparatus 400 may further include selectively a preprocessor 410, an option selector 420, an input interface 430, a storage 440, a communication interface 450, and an output interface 460, in addition to a spectrum obtainer 110 and a processor 120. Here, the spectrum obtainer 110 and the processor 120 are described above with reference to FIGS. 1 to 3, such that detailed description thereof will be omitted. Further, FIG. 4 illustrates the preprocessor 410 and the option selector 420 as separate parts from the processor 120, this is merely exemplary for convenience of explanation, and the preprocessor 410 and the option selector 420 may be configured as a part of the processor 120.

The preprocessor 410 may remove noise, which occurs by components other than a target component, from the first biological spectrum and the second biological spectrum. In one exemplary embodiment, the preprocessor 310 may use various noise removal methods, such as asymmetric least square (ALS), detrend, multiplicative scatter correction (MSC), extended multiplicative scatter correction (EMSC), standard normal variate (SNV), mean centering (MC), fourier transform (FT), orthogonal signal correction (OSC). Savitzky-Golay smoothing (SG), and the like, which are merely exemplary, and the noise removal method is not limited thereto.

The option selector 420 may select one of a plurality of options related to a method of extracting an individualized unit spectrum. In particular, the plurality of options include a first option of extracting an individualized unit spectrum by using principal component analysis (PCA), a second option of extracting an individualized unit spectrum by using independent component analysis (ICA), a third option of extracting an individualized unit spectrum by using non-negative matrix factorization (NMF), a fourth option of extracting an individualized unit spectrum by using auto-encoding (AE), and a fifth option of extracting an individualized unit spectrum by subtracting the first biological spectrum from the second biological spectrum. In this case, the processor 120 may extract an individualized unit spectrum from the first biological spectrum and the second biological spectrum by using at least one of the plurality of options.

The input interface 430 may receive input of various operation signals from a user. In one exemplary embodiment, the input interface 430 may include a keypad, a dome switch, a touch pad (static pressure/capacitance), a jog wheel, a jog switch, a hardware (H/W) button, and the like. Particularly, the touch pad, which forms a layer structure with a display, may be called a touch screen.

The storage 440 may store programs or commands for operation of the apparatus 400, and may store data input to and output from the apparatus 400. Further, the storage 440 may store the first biological spectrum data and the second biological spectrum data which are obtained by the spectrum obtainer 110, an individualized unit spectrum data extracted by the processor 120, a unit spectrum data of a target component, and the like.

The storage 440 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like. Further, the apparatus 400 may operate an external storage medium, such as web storage and the like, which performs a storage function of the storage 440 on the Internet.

The communication interface 450 may perform communication with an external device. For example, the communication interface 450 may transmit, to the external device, data input by a user through the input interface 430, the first biological spectrum data and the second biological spectrum data which are obtained by the spectrum obtainer 110, the individualized unit spectrum data extracted by the processor 120, the unit spectrum data of a target component, and the like, or may receive, from the external device, various data useful for extracting an individualized unit spectrum.

In this case, the external device may be medical equipment using the first biological spectrum data and the second biological spectrum data which are obtained by the spectrum obtainer 110, the individualized unit spectrum data extracted by the processor 120, the unit spectrum data of a target component, and the like, a printer to print out results, or a display to display the extracted individualized unit spectrum data. In addition, the external device may be a digital TV, a desktop computer, a cellular phone, a smartphone, a tablet PC, a laptop computer, a personal digital assistant (PDA), a portable multimedia player (PMP), a navigation, an MP3 player, a digital camera, a wearable device, and the like, but is not limited thereto.

The communication interface 450 may communicate with an external device by using Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. However, this is merely exemplary and is not intended to be limiting.

The output interface 460 may output the first biological spectrum data and the second biological spectrum data which are obtained by the spectrum obtainer 110, the individualized unit spectrum data extracted by the processor 120, the unit spectrum data of a target component, and the like. In one exemplary embodiment, the output interface 460 may output the first biological spectrum data and the second biological spectrum data which are obtained by the spectrum obtainer 110, the individualized unit spectrum data extracted by the processor 120, the unit spectrum data of a target component, and the like by using at least one of an acoustic method, a visual method, and a tactile method. To this end, the output interface 460 may include a display, a speaker, a vibrator, and the like.

Figure 5:
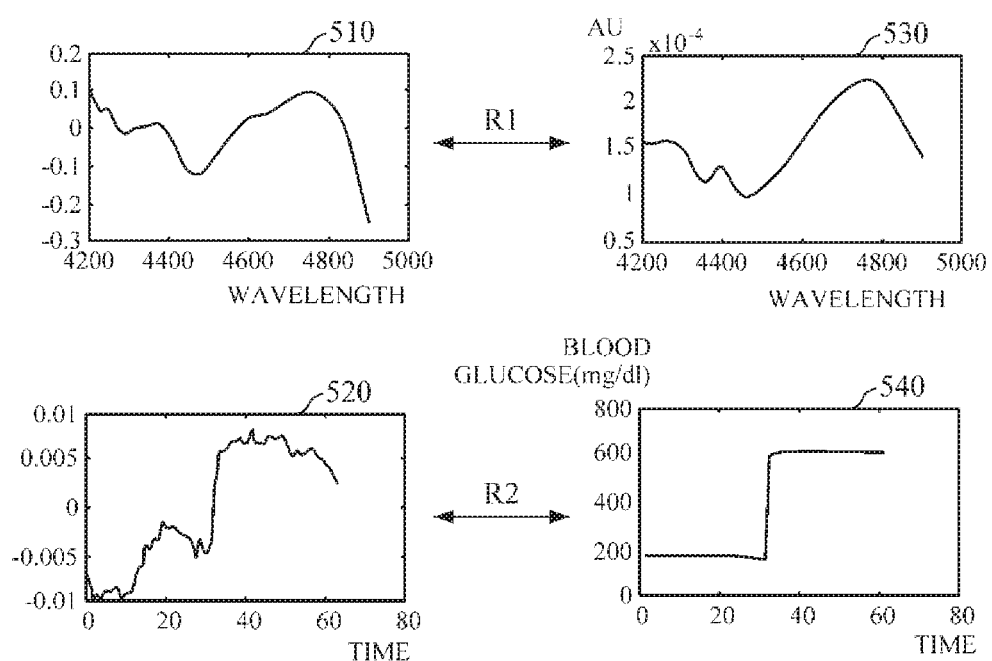
FIG. 5 illustrates a diagram explaining extracting an individualized unit spectrum by using principal component analysis (PCA) according to an exemplary embodiment.

FIG. 5 illustrates a diagram explaining extracting an individualized unit spectrum by using principal component analysis (PCA) according to an exemplary embodiment. For convenience of explanation, it is assumed in FIG. 5 that one candidate spectrum is extracted.

Referring to FIGS. 2 and 5, the candidate spectrum extractor 210 extracts, as a candidate spectrum, an eigenvector 510 of a first principal component based on the first biological spectrum and the second biological spectrum.

The candidate spectrum selector 220 may determine a similarity R1 between the eigenvector 510 of the first principal component and a unit spectrum 530 of a target component, and may determine whether the similarity R1 exceeds the first threshold. The unit spectrum 530 may be experimentally derived in advance and stored in the storage 440. Further, the candidate spectrum selector 220 may determine a similarity R2 between the eigenvalue 520 of the first principal component and a step function 540, and may determine whether the similarity R2 exceeds the second threshold. The processor 120 may use the step function 540 to approximate or estimate a glucose level change in reality, may be obtained by measuring a change in blood glucose concentrations over time in a step function.

In the case where the similarity R1 exceeds the first threshold, and the similarity R2 exceeds the second threshold, the candidate spectrum selector 220 may select the eigenvector 510 of the first principal component as a candidate spectrum associated with a target component.

The individualized unit spectrum extractor 230 may scale the eigenvector 510 of the first principal component to correspond to the unit spectrum 530, and may determine the scaled eigenvector as an individualized unit spectrum. In order to make the eigenvector 510 correspond to the unit spectrum 530, the individualized unit spectrum extractor 230 may scale the eigenvector 510 by adjusting an amplitude of the eigenvector 510 to match the amplitude of the unit spectrum 530. The scaled eigenvector 510 have substantially the same waveform as the original eigenvector 510, but may have a different amplitude from the original eigenvector 510.

Although it is assumed in FIG. 5 that one candidate spectrum is extracted, this is merely exemplary for convenience of explanation, and the extraction is not limited to one candidate spectrum. That is, the candidate spectrum extractor 210 may extract eigenvectors of the first principal component to an n-th principal component, which are generated by using PCA, as candidate spectrums; and the candidate spectrum selector 220 may select one eigenvector as a candidate spectrum associated with a target component by determining similarity between each of the eigenvectors of the first principal component to the n-th principal component and the unit spectrum 530, and by determining similarity between each of the eigenvectors of the first principal component to the n-th principal component and the step function 540. In this case, 'n' may be set to various values according to performance and purpose of use of a system.

The eigenvector may be referred to as a loading vector, a latent variable, a principal component, and the like, and the eigenvalue may be referred to as a loading score and the like.

Figure 6:
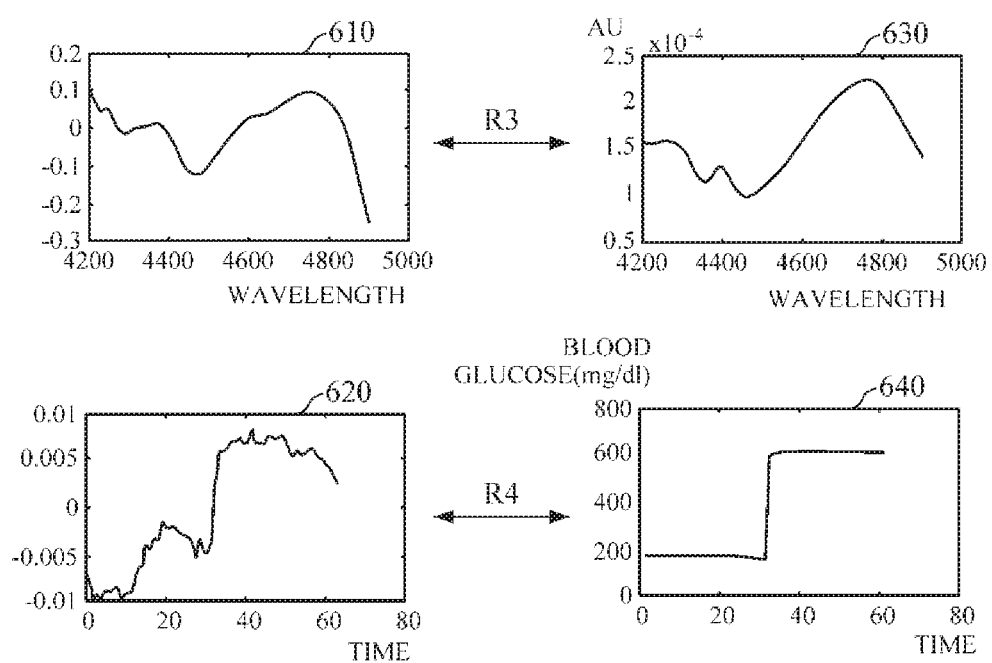
FIG. 6 is a diagram explaining extracting an individualized unit spectrum by using auto-encoding (AE) according to an exemplary embodiment.

FIG. 6 is a diagram explaining extracting an individualized unit spectrum by using auto-encoding (AE) according to an exemplary embodiment. For convenience of explanation, it is assumed in FIG. 6 that one candidate spectrum is extracted.

Referring to FIGS. 2 and 6, the candidate spectrum extractor 210 extracts a weight vector 610 as a candidate spectrum based on the first biological spectrum and the second biological spectrum, by using AE such as, for example, denoising auto-encoding, sparse auto-encoding, variational auto-encoding, and contractive auto-encoding.

The candidate spectrum selector 220 determines a similarity R3 between the weight vector 610 and a unit spectrum 630 of a target component, and determines whether the similarity R3 exceeds a third threshold. The unit spectrum 630 may be experimentally derived in advance and may have the same value as the unit spectrum 530. Further, the candidate spectrum selector 220 determines a similarity R4 between a value 620, obtained by multiplying an input data and the weight vector 610, and a step function 640, and determines whether the similarity R4 exceeds a fourth threshold. The input data may refer to data which are inputted to perform the AE, such as the first biological spectrum and the second biological spectrum. The step function 640 may have substantially the same function as the step function 540.

In the case where the similarity R3 exceeds the third threshold, and the similarity R4 exceeds the fourth threshold, the candidate spectrum selector 220 selects the weight vector 610 as a candidate spectrum associated with a target component.

The individualized unit spectrum extractor 230 scales the weight vector 610 to correspond to the unit spectrum 630, and extracts the scaled weight vector as an individualized unit spectrum.

Although it is assumed in FIG. 6 that one candidate spectrum is extracted, this is merely exemplary for convenience of explanation, and the extraction is not limited to one candidate spectrum. That is, similarly to FIG. 5, the candidate spectrum extractor 210 may extract, as a candidate spectrum, a plurality of weight vectors by using AE.

Figure 7:
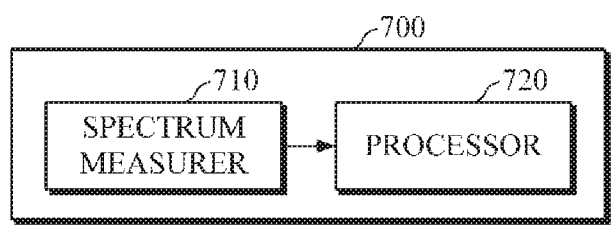
FIG. 7 is a block diagram illustrating an apparatus for estimating a biological component according to an exemplary embodiment.

FIG. 7 is a block diagram illustrating an apparatus for estimating a biological component according to exemplary embodiment. The biological component estimating apparatus 700 may be embedded in an electronic device. In particular, examples of the electronic device may include a cellular phone, a smartphone, a tablet PC, a laptop computer, a personal digital assistant (PDA), a portable multimedia player (PMP), a navigation, an MP3 player, a digital camera, a wearable device, and the like; and examples of the wearable device may include a wristwatch-type wearable device, a wristband-type wearable device, a ring-type wearable device, a waist belt-type wearable device, a necklace-type wearable device, an ankle band-type wearable device, a thigh band-type wearable device, a forearm band-type wearable device, and the like. However, the electronic device is not limited thereto, and the wearable device is neither limited thereto.

Referring to FIG. 7, the biological component estimating apparatus 700 includes a spectrum measurer 710 and a processor 720.

The spectrum measurer 710 may measure a biological spectrum from skin of a user. The spectrum measurer 710 may measure the biological spectrum by emitting light onto the skin and by receiving light reflected or scattered from the skin according to a predetermined control signal. In one exemplary embodiment, the spectrum measurer 710 may use infrared spectroscopy or Raman spectroscopy, but is not limited thereto, and may measure a spectrum by using various spectroscopy techniques.

The processor 720 may process various operations associated with estimation of a user's biological component by analyzing the measured biological spectrum data. Here, the biological component may include a blood component, including blood glucose, cholesterol, triglyceride, proteins, uric acid, and the like, and a skin component including collagen, keratin, elastin, and the like.

Hereinafter, for convenience of explanation, the following description will be made based on an example where a biological component is blood glucose.

The processor 720 may estimate a user's blood glucose value based on the measured biological spectrum and an individualized unit spectrum. In particular, a method of obtaining the individualized unit spectrum is described above with reference to FIGS. 1 to 6, such that detailed description thereof will be omitted.

In one exemplary embodiment, the processor 720 may estimate a blood glucose value by using the following Equations 1 and 2.

$$BS = Sm - Sb \qquad \text{[Equation 1]}$$

$$BG = RG + \frac{BS}{Su} \qquad \text{[Equation 2]}$$

Herein, Sm denotes the measured biological spectrum. Sb denotes a background spectrum. BS denotes a biological spectrum from which the background spectrum is removed, SU denotes the individualized unit spectrum, RG denotes a reference blood glucose value, and BG denotes the estimated blood glucose value. In this case, the background spectrum Sb may be spectrums measured continuously at regular intervals for a predetermined period of time in a reference state (e.g., when there is a small amount of blood glucose in a body, i.e., in an empty stomach state), and the reference state may be defined differently for each user according to user characteristics and the like. The reference blood glucose value RG may refer to a blood glucose value in a fasting state.

That is, once the biological spectrum Sm is measured for estimating a blood glucose value, the processor 720 may remove noise, caused by a component other than blood glucose, by subtracting the background spectrum Sb from the biological spectrum Sm, in order to increase a signal to noise ratio (SNR). Further, the processor 720 may estimate a blood glucose variation value $$\frac{BS}{Su}$$

based on the biological spectrum BS, from which noise (background spectrum) is removed, and the individualized unit spectrum SU, and may calculate the estimated blood glucose value by adding the reference blood glucose value RG to the estimated blood glucose variation value $$\frac{BS}{Su}.$$

As the biological component estimating apparatus 700 estimates a biological component by using an individualized unit spectrum in consideration of optical characteristics of each spectrum, the biological component estimating apparatus 700 may estimate a biological component of a user more accurately.

Figure 8:
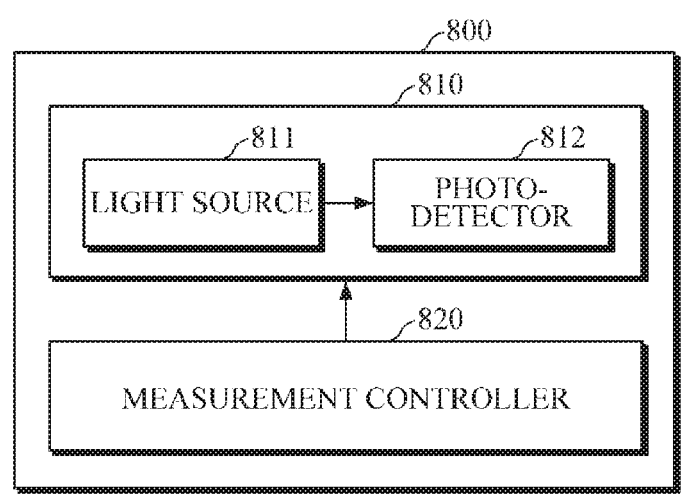
FIG. 8 is a block diagram illustrating a spectrum measuring apparatus according to an exemplary embodiment.

FIG. 8 is a block diagram illustrating a spectrum measuring apparatus according to an exemplary embodiment.

The spectrum measuring apparatus 800 may be an example of the spectrum measurer 710 of FIG. 7.

Referring to FIG. 8, the spectrum measuring apparatus 800 includes a spectrometer 810 and a measurement controller 820.

The spectrometer 810 may include a light source 811 to emit light onto a user's skin, and a photodetector 812 to obtain a skin spectrum by receiving light reflected or scattered from the skin.

The light source 811 may emit near infrared rays (NIR) or mid infrared rays (MIR) onto the user's skin. However, wavelengths of light to be emitted by the light source 811 may vary according to a purpose of measurement or the types of target component to be analyzed. Further, the light source 811 may include a single light-emitting body, or may be formed as an array of a plurality of light-emitting bodies. The light source 811 may be a light emitting diode (LED), a laser diode, a fluorescent body, and the like.

The photodetector 812 may include a photo diode, a photo transistor (PTr), a charge-coupled device (CCD), and the like. The photodetector 812 may include a single device, or may be formed as an array of a plurality of devices.

There may be various numbers and arrangements of the light source 811 and the photodetector 812, and the number and arrangement thereof may vary according to the types of target component, a purpose of use, the size and shape of the electronic device in which the spectrum measuring apparatus 800 is embedded, and the like.

The user's skin, onto which light is emitted, may be an area on a wrist that is adjacent to the radial artery. In the case where the area is the skin surface of the wrist where the radial artery passes, measurement may be relatively less affected by external factors, such as the thickness of a skin tissue in the wrist, which may cause errors in measurement. However, the object is not limited thereto, and may be a peripheral body part of the human body, such as fingers, toes, and the like, where blood vessels are densely located.

The measurement controller 820 may control the spectrometer 810 by generating a control signal according to a user's command or predetermined criteria.

In one exemplary embodiment, the measurement controller 820 may be connected to a healthcare instrument (e.g., a probe) in which the spectrum measuring apparatus 800 is mounted, and may generate a control signal to control the spectrometer 810 by receiving a command for measuring a spectrum which is received through the instrument. In this case, the command for measuring a spectrum may be a command for measuring a biological spectrum for estimating a biological component, or a command for measuring a background spectrum for use in noise removal.

In another exemplary embodiment, measurement criteria of a biological spectrum for estimating a biological component or a background spectrum may be preset, and the measurement controller 820 may automatically generate a control signal for controlling the spectrometer 810 according to the set criteria. For example, a time or an interval of estimating blood glucose levels may be preset for users, such as diabetic patients, for whom it is highly important to manage their blood glucose level, so that blood glucose levels may be estimated at a regular time or at regular intervals in an empty stomach state or after intake of sugar. Further, a measurement interval of a background spectrum, which is measured to remove noise from the measured biological spectrum, may be preset.

The measurement controller 820 is described as a part of the spectrum measuring apparatus 800, but is not limited thereto. That is, the measurement controller 820 may be configured as a part of the processor 720 of FIG. 7.

Figure 9:
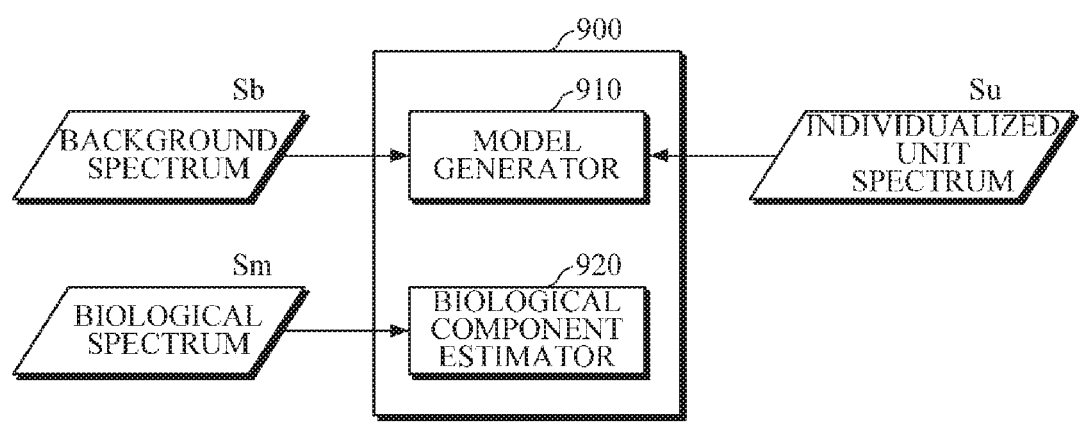
FIG. 9 is a block diagram illustrating a processor according to another exemplary embodiment.

FIG. 9 is a block diagram illustrating a processor according to an exemplary embodiment. The processor 900 of FIG. 9 may be an example of the processor 720 of FIG. 7.

Referring to FIG. 9, the processor 900 includes a model generator 910 and a biological component estimator 920.

The model generator 910 may generate a biological component estimation model for use in estimating a biological component. The model generator 910 may generate a biological component estimation model or may update an existing biological component estimation model by using a background spectrum Sb and an individualized unit spectrum Su.

In one exemplary embodiment, the model generator 910 may generate a blood glucose estimation model, represented by the following Equation 3, by using Beer Lambert's Law. However, the blood glucose estimation model of Equation 3 is merely exemplary, and the model is not limited thereto.

$$Sm = (Sb1 + Sb2 + Sb3 + Sb4 + \ldots) + \varepsilon_g \cdot L \cdot Cg \qquad [\text{Equation 3}]$$

Herein, Sm denotes a user's biological spectrum measured for estimating blood glucose, (Sb1+Sb2+Sb3+Sb4+ . . . ) denotes background spectrums measured for a predetermined period of time, $\varepsilon_g$ denotes an individualized unit spectrum for blood glucose, L denotes a light travel length while the biological spectrum Sm is measured or a light travel length estimated by using an aqueous path length, and Cg denotes a blood glucose variation value of a user.

The biological component estimator 920 may estimate a biological component of a user by using the measured biological spectrum and the biological component estimation model.

In one exemplary embodiment, the biological component estimator 920 may calculate the blood glucose variation value Cg of a user by substituting the biological spectrum Sm in Equation 3, and may calculate an estimated blood glucose value by adding a reference blood glucose value to the blood glucose variation value Cg (see Equation 2).

Figure 10:
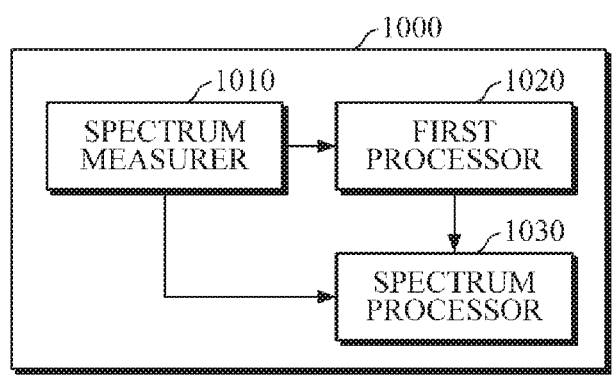
FIG. 10 is a block diagram illustrating an apparatus for estimating a biological component according to another exemplary embodiment.

FIG. 10 is a block diagram illustrating an apparatus for estimating a biological component according to another exemplary embodiment. The biological component estimating apparatus 1000 may be embedded in an electronic device. In particular, examples of the electronic device may include a cellular phone, a smartphone, a tablet PC, a laptop computer, a personal digital assistant (PDA), a portable multimedia player (PMP), a navigation, an MP3 player, a digital camera, a wearable device, and the like; and examples of the wearable device may include a wristwatch-type wearable device, a wristband-type wearable device, a ring-type wearable device, a waist belt-type wearable device, a necklace-type wearable device, an ankle band-type wearable device, a thigh band-type wearable device, a forearm band-type wearable device, and the like. However, the electronic device is not limited thereto, and the wearable device is neither limited thereto.

Referring to FIG. 10, the biological component estimating apparatus 1000 includes a spectrum measurer 1010, a first processor 1020, and a second processor 1030.

The spectrum measurer 1010 may perform the function of the spectrum obtainer 110 of FIG. 1 and the function of the spectrum measurer 710 of FIG. 7, the first processor 1020 may perform the function of the processor 120 of FIG. 1, and the second processor 1030 may perform the function of the processor 720 of FIG. 7. That is, the apparatus 1000 for estimating a biological component is configured by integrating the apparatus 100 for obtaining an individualized unit spectrum of FIG. 1 and the apparatus 700 for estimating a biological component of FIG. 7.

Although FIG. 10 illustrates the first processor 1020 and the second processor 1030 as separate parts, the first processor 1020 and the second processor 1030 may be integrated into a single processor.

Figure 11:
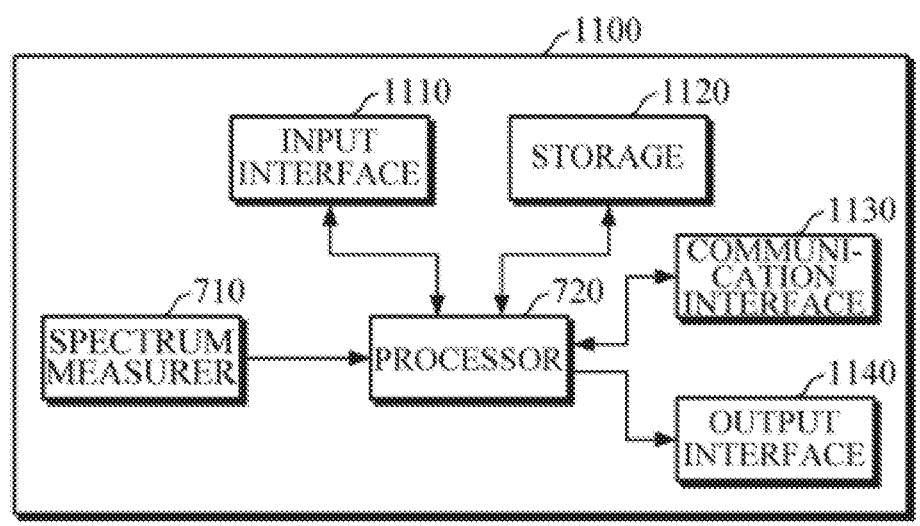
FIG. 11 is a block diagram illustrating an apparatus for estimating a biological component according to another exemplary embodiment.

FIG. 11 is a block diagram illustrating yet another example of an apparatus for estimating a biological component.

Referring to FIG. 11, the biological component estimating apparatus 1100 includes a spectrum measurer 710, a processor 720, an input interface 1110, a storage 1120, a communication interface 1130, and an output interface 1140. Here, the spectrum measurer 710 and the processor 720 are described above with reference to FIGS. 7 to 9, such that detailed description thereof will be omitted.

The input interface 1110 may receive input of various operation signals from a user. In one exemplary embodiment, the input interface 1110 may include a keypad, a dome switch, a touch pad (static pressure/capacitance), a jog wheel, a jog switch, a hardware (H/W) button, and the like. Particularly, the touch pad, which forms a layer structure with a display, may be called a touch screen.

The storage 1120 may store programs or commands for operation of the apparatus 1100 for estimating a biological component, and may store data input to and output from the apparatus 1100 for estimating a biological component. Further, the storage 1120 may store biological spectrum data measured by the spectrum measurer 710, estimated biological component data estimated by the processor 720, individualized unit spectrum data of a biological component, background spectrum data, biological component estimation model data, and the like.

The storage 1120 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like. Further, the apparatus 1100 for estimating a biological component may operate an external storage medium, such as web storage and the like, which performs a storage function of the storage 1120 on the Internet.

The communication interface 1130 may perform communication with an external device. For example, the communication interface 1130 may transmit, to the external device, data input by a user through the input interface 1110, the biological spectrum data measured by the spectrum measurer 710, the estimated biological component data estimated by the processor 720, the individualized unit spectrum data of a biological component, the background spectrum data, the biological component estimation model data, and the like, or may receive, from the external device, various data useful for estimating a biological component.

In particular, the external device may be medical equipment using the biological spectrum data measured by the spectrum measurer 710, the estimated biological component data estimated by the processor 720, the individualized unit spectrum data of a biological component, the background spectrum data, the biological component estimation model data, and the like, a printer to print out results, or a display to display the results. In addition, the external device may be a digital TV, a desktop computer, a cellular phone, a smartphone, a tablet PC, a laptop computer, a personal digital assistant (PDA), a portable multimedia player (PMP), a navigation, an MP3 player, a digital camera, a wearable device, and the like, but is not limited thereto.

The communication interface 1130 may communicate with an external device by using Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. However, this is merely exemplary and is not intended to be limiting.

The output interface 1140 may output the biological spectrum data measured by the spectrum measurer 710, the estimated biological component data estimated by the processor 720, the individualized unit spectrum data of a biological component, the background spectrum data, the biological component estimation model data, and the like. In one exemplary embodiment, the output interface 1140 may output the biological spectrum data measured by the spectrum measurer 710, the estimated biological component data estimated by the processor 720, the individualized unit spectrum data of a biological component, the background spectrum data, the biological component estimation model data, and the like by using at least one of an acoustic method, a visual method, and a tactile method. To this end, the output interface 1140 may include a display, a speaker, a vibrator, and the like.

Figure 12:
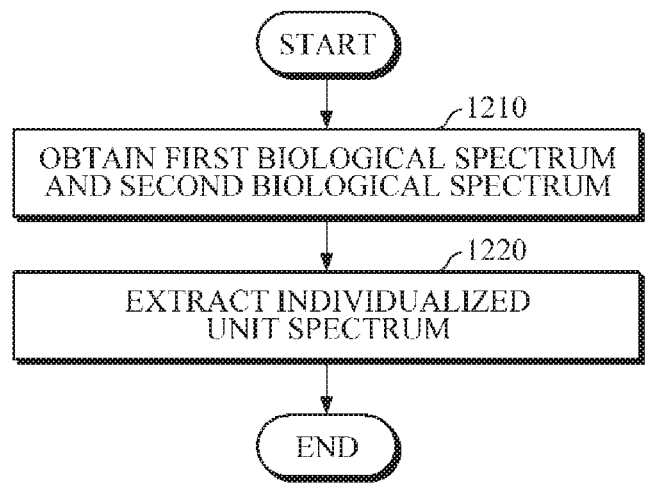
FIG. 12 is a flowchart illustrating a method of obtaining an individualized unit spectrum according to an exemplary embodiment.

FIG. 12 is a flowchart illustrating a method of obtaining an individualized unit spectrum according to an exemplary embodiment. The method of obtaining an individualized unit spectrum of FIG. 12 may be performed by the apparatus 100 for obtaining an individualized unit spectrum of FIG. 1.

Referring to FIGS. 1 and 12, the apparatus 100 for obtaining an individualized unit spectrum may obtain a first biological spectrum, which is measured when there is a small amount of a target component in a body, and a second biological spectrum which is measured when there is a large amount of a target component in a body in operation 1210.

For example, the apparatus 100 may obtain the first biological spectrum and the second biological spectrum from an external device which measures and/or stores biological spectrums. Alternatively, the apparatus 100 may obtain the first biological spectrum and the second biological spectrum by emitting light onto skin and by receiving light reflected or scattered from the skin. In particular, the apparatus 100 may measure the first biological spectrum when the user's stomach is empty (e.g., two hours after the user consumes food), and may measure the second biological spectrum when the user's stomach is full or almost full (e.g., within 30 minutes after the user consumes food).

The apparatus 100 may extract an individualized unit spectrum, corresponding to a unit spectrum of a target component, from the obtained first biological spectrum and second biological spectrum in operation 1220. For example, the processor 120 may extract the individualized unit spectrum from the first biological spectrum and the second biological spectrum by using a feature extraction method, or may extract an individualized unit spectrum by subtracting the first biological spectrum from the second biological spectrum.

Figure 13:
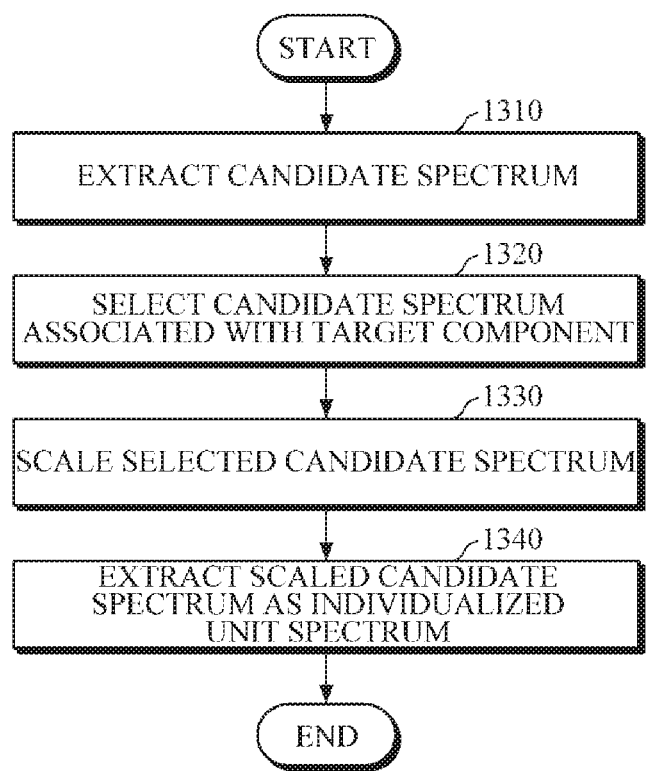
FIG. 13 is a block diagram illustrating a method of extracting an individualized unit spectrum according to an exemplary embodiment.

FIG. 13 is a block diagram illustrating a method of extracting an individualized unit spectrum according to an exemplary embodiment. The method of extracting an individualized unit spectrum may be an example of the extraction of an individualized unit spectrum in operation 1220 of FIG. 12.

Referring to FIGS. 1 and 13, the apparatus 100 may extract at least one candidate spectrum from the first biological spectrum and the second biological spectrum by using a feature extraction method in operation 1310. In this case, as described above, the feature extraction method may include principal component analysis (PCA), independent component analysis (ICA), non-negative matrix factorization (NMF), auto-encoding (AE), and the like.

The apparatus 100 may select a candidate spectrum, associated with a target component, from among the extracted at least one candidate spectrum in operation 1320. In one exemplary embodiment, the apparatus 100 may select, as a candidate spectrum associated with a target component, a candidate spectrum which satisfies predetermined requirements based on the shape of a candidate spectrum and/or a variation over time in a candidate spectrum. In particular, the predetermined requirements may include a requirement for a similarity (hereinafter referred to as first similarity) between a candidate spectrum and a unit spectrum of a target component to exceed a predetermined threshold (hereinafter referred to as a first threshold), a similarity (hereinafter referred to as second similarity) between a variation over time in a candidate spectrum and a step function to exceed a predetermined threshold (hereinafter referred to as a second threshold), a requirement of a value obtained by multiplying the first similarity and the second similarity to exceed a predetermined threshold (hereinafter referred to as a third threshold), and the like.

In particular, the apparatus 100 may use a similarity calculation method, such as Euclidean distance, Manhattan Distance, Cosine Distance. Mahalanobis Distance, Jaccard Coefficient. Extended Jaccard Coefficient, Pearson's Correlation Coefficient, Spearman's Correlation Coefficient, and the like, or a statistical test such as f-test, t-test, z-test, and the like.

The apparatus 100 may scale the selected candidate spectrum to correspond to a unit spectrum of a target component in operation 1330, and may extract the scaled candidate spectrum as an individualized unit spectrum in operation 1340.

Upon selecting a plurality of candidate spectrums in operation 1320, the apparatus 100 may generate an average candidate spectrum by averaging the selected plurality of candidate spectrums, and may scale the generated average candidate spectrum to correspond to a unit spectrum.

Figure 14:
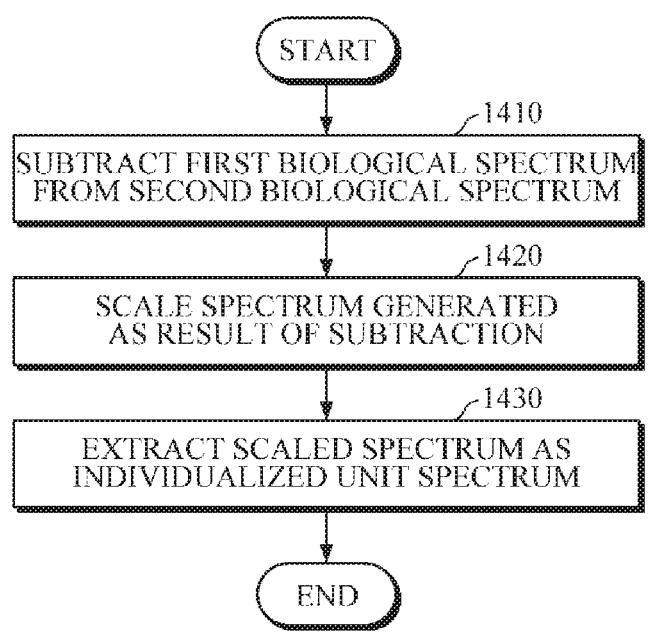
FIG. 14 is a block diagram illustrating a method of extracting an individualized unit spectrum according to another exemplary embodiment.

FIG. 14 is a block diagram illustrating a method of extracting an individualized unit spectrum according to another exemplary embodiment. The method of extracting an individualized unit spectrum of FIG. 14 may be another example of the extraction of an individualized unit spectrum in operation 1220 of FIG. 12.

Referring to FIGS. 1 and 14, the apparatus 100 may subtract the first biological spectrum from the second biological spectrum in operation 1410. In one exemplary embodiment, in the case where there are a plurality of second biological spectrum and a plurality of first biological spectrum, the apparatus 100 may calculate an average second biological spectrum and an average first biological spectrum, and may subtract the calculated average first biological spectrum from the calculated average second biological spectrum.

The apparatus 100, generated as a result of the subtraction in operation 1410, to correspond to a unit spectrum of a target component in operation 1420, and may extract the scaled spectrum as the individualized unit spectrum in operation 1430.

Figure 15:
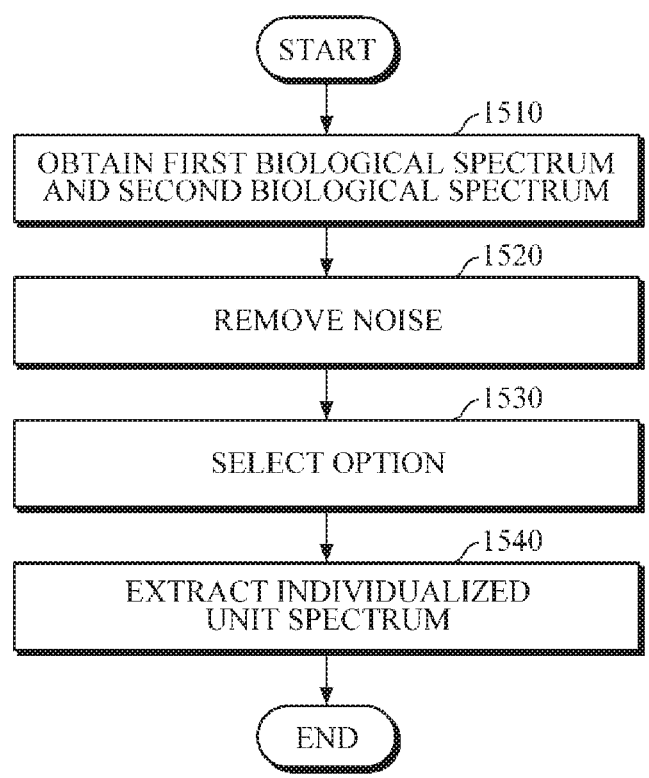
FIG. 15 is a flowchart illustrating a method of obtaining an individualized unit spectrum according to another exemplary embodiment.

FIG. 15 is a flowchart illustrating a method of obtaining an individualized unit spectrum according to another exemplary embodiment. The method of obtaining an individualized unit spectrum of FIG. 15 may be performed by the apparatus 400 for obtaining an individualized unit spectrum of FIG. 4.

Referring to FIGS. 4 and 15, the apparatus 400 may obtain the first biological spectrum and the second biological spectrum in operation 1510, and may remove noise, which occurs by a component other than a target component, from the first biological spectrum and the second biological spectrum in operation 1520. In one embodiment, the apparatus 400 may use various noise removal methods, such as asymmetric least square (ALS), detrend, multiplicative scatter correction (MSC), extended multiplicative scatter correction (EMSC), standard normal variate (SNV), mean centering (MC), fourier transform (FT), orthogonal signal correction (OSC), Savitzky-Golay smoothing (SG), and the like, which are merely exemplary, and the noise removal method is not limited thereto.

The apparatus 400 may select one of a plurality of options related to a method of extracting an individualized unit spectrum in 1530. In this case, the plurality of options include a first option of extracting an individualized unit spectrum by using principal component analysis (PCA), a second option of extracting an individualized unit spectrum by using independent component analysis (ICA), a third option of extracting an individualized unit spectrum by using non-negative matrix factorization (NMF), a fourth option of extracting an individualized unit spectrum by using auto-encoding (AE), and a fifth option of extracting an individualized unit spectrum by subtracting the first biological spectrum from the second biological spectrum.

The apparatus 400 may extract an individualized unit spectrum from the first biological spectrum and the second biological spectrum in operation 1540 by using a method of an option selected in operation 1530.

Figure 16:
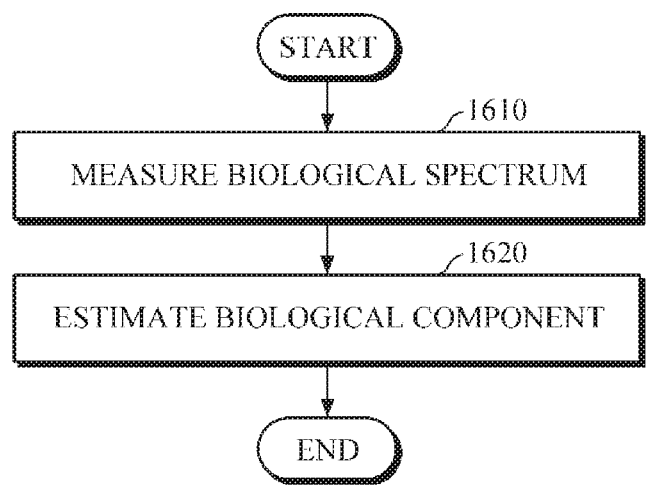
FIG. 16 is a flowchart illustrating a method of estimating a biological component according to an exemplary embodiment.

FIG. 16 is a flowchart illustrating an example of a method of estimating a biological component. The method of estimating a biological component of FIG. 16 may be performed by the apparatus 700 for estimating a biological component of FIG. 7.

Referring to FIGS. 7 and 16, the biological component estimating apparatus 700 may measure a biological spectrum from skin of a user. For example, the biological component estimating apparatus 700 may measure a biological spectrum by emitting light onto the skin and by receiving light reflected or scattered from the skin in operation 1610.

The biological component estimating apparatus 700 may estimate a blood glucose value of a user based on the measured spectrum and an individualized unit spectrum in operation 1620.

While not restricted thereto, an exemplary embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an exemplary embodiment may be written as a computer program transmitted over a computer-readable transmission medium, such as a carrier wave, and received and implemented in general-use or special-purpose digital computers that execute the programs. Moreover, it is understood that in exemplary embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An apparatus for obtaining an individualized unit spectrum, the apparatus comprising:
   a spectrometer configured to obtain a first biological spectrum from a subject in a fasting state, and obtain a second biological spectrum from the subject in a non-fasting state; and
   a processor configured to:
   extract a plurality of candidate spectrums from the first biological spectrum;
   determine similarities between each of the plurality of candidate spectrums and a predetermined unit spectrum of a target component, throughout a continuous waveform of each of the plurality of candidate spectrums and a continuous waveform of the predetermined unit spectrum;
   select, among the plurality of candidate spectrums, a candidate spectrum whose similarity to the predetermined unit spectrum is greater than a preset threshold; and
   convert the selected candidate spectrum to the individualized unit spectrum to be used to estimate the target component of the subject, based on the predetermined unit spectrum.

2. The apparatus of claim 1, wherein the processor is further configured to extract the plurality of candidate spectrums based on at least one of principal component analysis (PCA), independent component analysis (ICA), non-negative matrix factorization (NNW), and auto-encoding (AE).

3. The apparatus of claim 1, wherein the processor is further configured to:
   scale the selected candidate spectrum based on the predetermined unit spectrum, and extract the scaled candidate spectrum as the individualized unit spectrum.

4. The apparatus of claim 3, wherein the processor is further configured to select the candidate spectrum based on at least one of a shape of the candidate spectrum and a variation over time in the candidate spectrum.

5. The apparatus of claim 4, wherein the processor is further configured to select the candidate spectrum in response to the candidate spectrum satisfying at least one of a first condition under which a first similarity between the candidate spectrum and the predetermined unit spectrum exceeds a first threshold, a second condition under which a second similarity between a variation over time in the candidate spectrums and a step function exceeds a second threshold, and a third condition under which a product of the first similarity and the second similarity exceeds a third threshold.

6. The apparatus of claim 3, wherein the processor is further configured to use a similarity calculation method or a statistical test,
   wherein the similarity calculation method comprises at least one of Euclidean distance, Manhattan Distance, Cosine Distance, Mahalanobis Distance, Jaccard Coefficient, Extended Jaccard Coefficient, Pearson's Correlation Coefficient, and Spearman's Correlation Coefficient, and
   wherein the statistical test comprises at least one of f-test, t-test, and z-test.

7. The apparatus of claim 3, wherein in response to at least wo of the plurality of candidate spectrums being selected, the processor is further configured to generate an average candidate spectrum by averaging the selected at least two candidate spectrums, and scale the generated average candidate spectrum to correspond to the predetermined unit spectrum.

8. The apparatus of claim 1, wherein the processor is further configured to remove noise from the first biological spectrum and the second biological spectrum.

9. The apparatus of claim 8, wherein the processor is further configured to use at least one of asymmetric least square (ALS), detrend, multiplicative scatter correction (MSC), extended multiplicative scatter correction (EMSC), standard normal variate (SNV), mean centering (MC), fourier transform (FT), orthogonal signal correction (OSC), and Savitzky-Golay smoothing (SG).

10. The apparatus of claim 1, wherein the processor is further configured to:
    subtract the first biological spectrum from the second biological spectrum to obtain a subtracted spectrum; and
    scale the subtracted spectrum to correspond to the predetermined unit spectrum of the target component, and extract the scaled subtracted spectrum as the individualized unit spectrum.

11. The apparatus of claim 1, wherein the processor is further configured to select a method from among:
    a first method of extracting the individualized unit spectrum using principal component analysis (PCA);
    a second method of extracting the individualized unit spectrum using independent component analysis (ICA);
    a third method of extracting the individualized unit spectrum using non-negative matrix factorization (NMF);
    a fourth method of extracting the individualized unit spectrum using auto-encoding (AE); and
    a fifth option of method the individualized unit spectrum by subtracting the first biological spectrum from the second biological spectrum, and
    wherein the processor is further configured to extract the individualized unit spectrum based on the selected method.

12. The apparatus of claim 1, wherein the target component comprises a blood component and a skin component of the subject,
    wherein the blood component comprises at least one of blood glucose, cholesterol, triglyceride, proteins, and uric acid; and
    the skin component comprises at least one of collagen, keratin, elastin, and body fat.

13. A method of obtaining an individualized unit spectrum, the method comprising:
    measuring a first biological spectrum from a subject in a fasting state, and measuring a second biological spectrum from the subject in a non-fasting state;

extracting a plurality of candidate spectrums from the first biological spectrum;
determining similarities between each of the plurality of candidate spectrums and a predetermined unit spectrum of a target component, throughout a continuous waveform of each of the plurality of candidate spectrums and a continuous waveform of the predetermined unit spectrum;
selecting, among the plurality of candidate spectrums, a candidate spectrum whose similarity to the predetermined unit spectrum is greater than a preset threshold;
converting the selected candidate spectrum to the individualized unit spectrum to be used to estimate the target component of the subject, based on the selected predetermined unit spectrum.

14. The method of claim 13, wherein the extracting the candidate spectrum comprises extracting the candidate spectrum based on at least one of principal component analysis (PCA), independent component analysis (ICA), non-negative matrix factorization (NMF), and auto-encoding (AE).

15. The method of claim 13, wherein the selecting the candidate spectrum associated with the target component comprises selecting the candidate spectrum based on at least one of a shape of the candidate spectrum and a variation over time in the candidate spectrum.

16. The method of claim 15, wherein the selecting the candidate spectrum associated with the target component comprises selecting the candidate spectrum in response to the candidate spectrum satisfying at least one of a first condition under which a first similarity between the candidate spectrum and the predetermined unit spectrum exceeds a first threshold, a second condition under which a second similarity between a variation over time in the candidate spectrum and a step function exceeds a second threshold, and a third condition under which a product of the first similarity and the second similarity exceeds a third threshold.

17. The method of claim 13, the selecting the candidate spectrum associated with the target component comprises selecting the candidate spectrum based on a similarity calculation method or a statistical test,
wherein the similarity calculation method comprises at least one of Euclidean distance, Manhattan Distance, Cosine Distance, Mahalanobis Distance, Jaccard Coefficient, Extended Jaccard Coefficient, Pearson's Correlation Coefficient, and Spearman's Correlation Coefficient, and
wherein the statistical test comprises at least one of f-test, t-test, and z-test.

18. The method of claim 13, wherein the scaling the selected candidate spectrum comprises, in response to at least two of the plurality of candidate spectrums being selected, generating an average candidate spectrum by averaging the selected at least two candidate spectrums, and scaling the generated average candidate spectrum to correspond to the predetermined unit spectrum.

19. The method of claim 13, further comprising removing noise from the first biological spectrum and the second biological spectrum.

20. The method of claim 19, wherein the removing the noise comprises removing the noise based on at least one of asymmetric least square (ALS), detrend, multiplicative scatter correction (MSC), extended multiplicative scatter correction (EMSC), standard normal variate (SNV), mean centering (MC), fourier transform (FT), orthogonal signal correction (OSC), and Savitzky-Golay smoothing (SG).

* * * * *